(12) United States Patent
Geissler et al.

(10) Patent No.: US 6,342,605 B1
(45) Date of Patent: Jan. 29, 2002

(54) VALERALDEHYDE AND PROCESS FOR ITS PREPARATION

(75) Inventors: Holger Geissler, Mainz (DE); Petrus W. N. M. van Leeuwen, Kockengen (NL); Paul C. J. Kamer, Naarden (NL); Lars A. van der Veen, Amsterdam (NL)

(73) Assignee: Celanese GmbH (DE)

( * ) Notice: Subject to any disclaimer, the term of this patent is extended or adjusted under 35 U.S.C. 154(b) by 0 days.

(21) Appl. No.: 09/376,909

(22) Filed: Aug. 18, 1999

(30) Foreign Application Priority Data

Aug. 26, 1998 (DE) .......................... 198 38 742

(51) Int. Cl.[7] .................. C07F 9/6541; C07F 9/655; C07F 9/02; C07F 17/02
(52) U.S. Cl. ................ 546/22; 549/26; 549/27; 549/359; 556/21; 556/22; 568/12
(58) Field of Search ............ 549/26, 27, 359; 568/12; 546/22; 556/22, 21

(56) References Cited

U.S. PATENT DOCUMENTS 5,508,438 A * 4/1996 Broger et al. ............... 549/216
5,516,944 A * 5/1996 Broger et al. ............... 549/216

FOREIGN PATENT DOCUMENTS

| EP | 0212639 | 3/1987 | ................. 549/216 |
| EP | 0530015 | 3/1993 | ................. 549/216 |
| WO | 9530680 | 11/1995 | ................. 549/216 |
| WO | 9733854 | 9/1997 | ................. 549/216 |

OTHER PUBLICATIONS

XP–002155413, Hobbs et al, pp. 4422–4427.
XP–000960496, van der Veen et al, pp. 336–338.
XP–000964505, van der Veen et al, pp. 4765–4777.

* cited by examiner

*Primary Examiner*—Alan L. Rotman
*Assistant Examiner*—Raymond Covington
(74) *Attorney, Agent, or Firm*—Bierman, Muserlian and Lucas

(57) ABSTRACT

Bidentate phosphine ligands of the formula $$\begin{array}{c} R3 \quad R4 \quad R1 \quad R2 \\ \diagdown \quad | \quad | \quad \diagup \\ X \quad P\!-\!E\!-\!P \quad X \\ \diagup \quad | \quad | \quad \diagdown \\ R2 \quad R1 \quad R4 \quad R3 \end{array}$$

wherein the substituents are as defined in the specification and a process for preparing linear aldehydes by hydroformylating internal olefins using such phosphine ligands.

16 Claims, No Drawings

VALERALDEHYDE AND PROCESS FOR ITS PREPARATION

SUMMARY OF THE INVENTION

Novel bidentate phosphine ligands and a process for preparing linear aldehydes by hydroformylating internal olefins using said phosphine ligands.

STATE OF THE ART

Linear aldehydes, particularly butyraldehyde, are of great industrial importance and, after further processing to the alcohols, are widely used in the plasticizer, solvent and polymer sector. Since mixtures of internal olefins, such as raffinate II, are produced in large amounts as a by-product in refining and cracking in the oil-processing industry, hydroformylating internal olefins to produce linear aldehydes is of great industrial interest.

The term "internal olefins" means those olefins which have at least one non-terminal double bond. However, this does not mean that internal olefins may not have a terminal double bond. Therefore, the term "internal olefin" is also taken to mean, for example, a compound such as 1,3-pentadiene.

It is known to prepare aldehydes by hydroformylating olefins using a catalyst with linear and branched aldehydes generally being formed simultaneously:

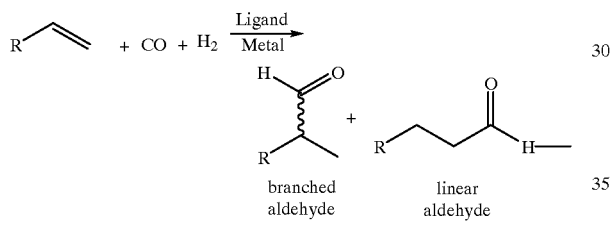

For a reaction of this type, bidentate ligands are also used as a catalyst component. In this case, for example, the ligand can be used together with a metal or in the form of a complex with a metal.

The term "bidentate ligand" means here and hereinafter molecules of the formula

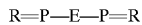

wherein, —P=R and R=P— are individually organic cyclic groups in which the phosphorous atoms are part of the cyclic system and are linked to the cyclic system via a phosphorus-carbon bond or a phosphorus-oxygen bond; and E is a bridging group which links the corresponding phosphorus atoms of the two organic cyclic groups.

For industrial hydroformylation reactions, a high selectivity for the linear or branched aldehydes is particularly necessary. This selectivity is generally expressed by what is termed the l/b ratio=(linear aldehyde)·(branched aldehyde)$^{-1}$. The hydroformylation is described by Frohning and Kohlpaintner in *Applied Homogeneous Catalysis with Organometallic Compounds*, Ed. B. Cornils, W. A. Hermann; VCH, Weinheim 1966, Vol. 1, pp. 29–104. Another example of the use of bidentate ligands in catalytic reactions is the hydrogenation described by Brunner in *Applied Homogeneous Catalysis with Organometallic Compounds*, Ed. B. Cornils, W. A. Hermann; VCH, Weinheim 1966, Vol. 1, pp. 201–219.

EP-0 530 015 A1 describes the use of ligands of the type R=P—E—P=R, such as the ligand of the formula

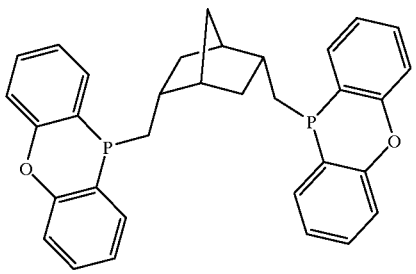

which are used in metal catalysts for the chiral synthesis of pharmaceuticals and novel intermediates. JP 07082281 A2 (JP 93-225998) discloses that ligands of this structural type can be used in hydroformylation for the synthesis of branched olefins with high selectivity.

Hopps describes in J. Organ. Chem., 1981, Vol 46, pp. 4422–4427, the use of a ligand of the type R=P—E—P=R, such as the ligand of the formula

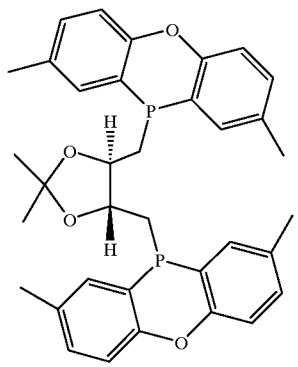

for the asymmetric hydroformylation of vinyl acetate, vinyl propionate and vinyl benzoate, the selectivity for the branched aldehydes being 75–95%.

EP-0 213 639 B1 describes a bidentate phosphite ligand of the type R=P—E—P=R, where P=R or R=P are individually organic cyclic groups in which the phosphorus atoms are part of the cyclic system and are linked to the cyclic system via a phosphorus-oxygen bond, and E is a bridging group which links the two phosphorus atoms of the two organic cyclic groups and where the phosphorus atom is linked to the bridging group E via a phosphorus-oxygen bond. These ligands are, for example, a ligand of the formula

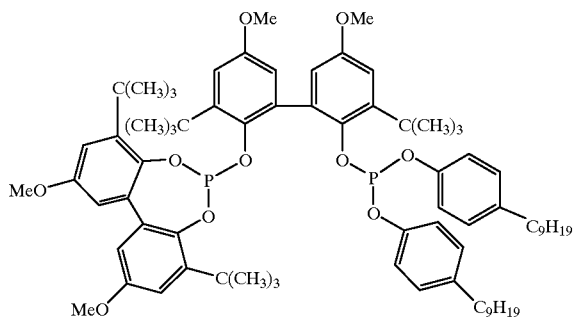

and can be used for hydroformylating internal olefins to produce linear aldehydes. The multistage synthesis of this ligand and the lower stability of phosphite ligands compared with phosphine ligands in general is, however, a disadvantage for industrial implementation.

OBJECTS OF THE INVENTION

It is an object of the invention to provide novel ligands and a process for hydroformylating internal olefins to produce linear aldehydes, which overcomes the disadvantages of the processes described for hydroformylating internal olefins and which converts internal olefins to produce linear aldehydes with high selectivity.

These and other objects of the invention will become obvious from the following detailed description.

THE INVENTION

The novel ligands of the invention are bidentate phosphine ligands of the formula

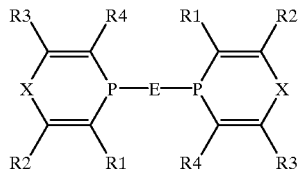

I wherein R1, R2, R3 and R4 are independently selected from the group consisting of hydrogen, fluorine, alkyl of 1 to 8 carbon atoms, alkoxy of 1 to 8 carbon atoms, acyloxy of an organic carboxylic acid of 1 to 8 carbon atoms, aryl of 6 to 18 carbon atoms, aryloxy of 6 to 18 carbon atoms, —CN, —$CF_3$, —CHO, —$SO_3H$, —$SO_3M$, —$SO_2R$, —SOR, —$NH_2$, —NH-alkyl of 1 to 8 carbon atoms, —N-alkyl$_2$ of 1 to 8 carbon atoms, —NHCO-alkyl, —N-(alkyl)-(Co-(alkyl) where the alkyl have 1 to 4 carbon atoms, —COO-alkyl of 1 to 8 carbon atoms, —$CONH_2$, —CO-alkyl of 1 to 8 carbon atoms, —NHCOH, —NHCOO-alkyl of 1 to 4 carbon atoms, —CO-aryl of 1 to 8 carbon atoms, —COO-aryl of 1 to 8 carbon atoms, —CHCH—$CO_2$-alkyl of 1 to 8 carbon atoms, —PO-(-aryl)$_2$ of 1 to 8 carbon atoms, —PO-(alkyl$_2$) of 1 to 4 carbon atoms; M is a cation selected from the group consisting of alkali metal ions, alkaline earth metal ions, —$NR_2H_2$, —$NR_3H$, —$NRH_3$, —$NR_4$, —$NH_4$, —$PR_2H_2$, —$PR_3H$, —$PRH_3$, —$PR_4$ and —$PH_4$; or R1, R2, R3 and R4, with one another, together form at least one aliphatic or aromatic ring of 5 to 20 carbon atoms; E is a bridge linking the two phosphorus atoms, where the number of atoms situated between the two phosphorus atoms is between 2 and 6, selected from the group consisting of C, N, Si, S, O, P, Fe and As; X is selected from the group consisting of —O—, —S—, —Si($R^a$)$_2$—, —Si(O$R^a$)$_2$—, —N(C(O)$R^a$)—, —N($R^b$)—, —C($R^c$) ($R^c$)—, —C(O)—, —N(Si$R^d$)—, —P($R^d$)—, —P(O)($R^d$)—, —C=C($R^c$) ($R^c$)— and —P(O$R^d$)— wherein $R^a$ is alkyl of 1 to 8 carbon atoms, $R^b$ is aryl of 6 to 18 carbon atoms, $R^c$ is selected from the group consisting of hydrogen, alkyl of 1 to 8 carbon atoms, aryl of 6 to 18 carbon atoms, alkoxy of 1 to 8 carbon atoms, aryloxy of 6 to 18 carbon atoms, $R^a$(O)— and $R^b$(O); and $R^d$ is one of $R^a$ or $R^b$.

According to a preferred embodiment, E is one of the following groups:

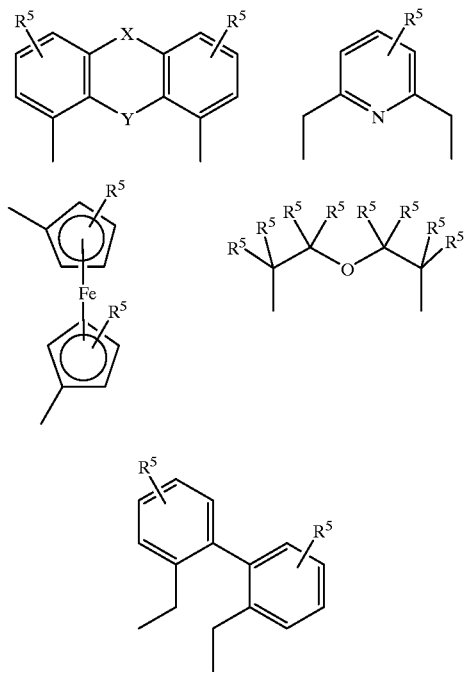

wherein X is selected from the group consisting of —O—, —S—, —Si($R^a$)$_2$—, —Si(O$R^a$)$_2$—, —N(C(O)$R^a$)—, —N($R^b$)—, —C($R^c$)($R^c$)—, —C(O)—, —N(Si$R^d$)—, —P($R^d$)—, —P(O) ($R^d$)—, —C=C($R^c$) ($R^c$)— and —P(O$R^d$)—, $R^a$ is alkyl of 1 to 8 carbon atoms $R^b$ is aryl of 6 to 18 carbon atoms $R^c$ is selected from the group consisting of hydrogen, alkyl of 1 to 8 carbon atoms, aryl of 6 to 18 carbon atoms, alkoxy of 1 to 8 carbon atoms, aryloxy of 6 to 18 carbon atoms, $R^a$(O)— or $R^b$(O)—; and $R^d$ is one of $R^a$ or $R^b$;

Y is oxygen or sulfur; and

R5s are individually aryl of 6 to 18 carbon atoms or alkyl of 1 to 8 carbon atoms.

In accordance with a further preferred embodiment of the invention, E is one of the following groups:

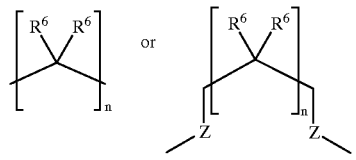

where R6 is alkyl of 1 to 8 carbon atoms or aryl of 6 to 18 carbon atoms; Z is between oxygen or nitrogen, and n is an integer of 2 to 6.

The phosphine ligands of the invention are used, in particular, in a process for preparing linear aldehydes by hydroformylating internal olefins of 4 to 12 carbon atoms in the presence of a bidentate phosphine ligand of the formula

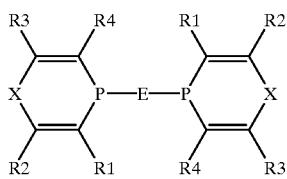

wherein R1, R2, R3, R4, M, E and X are defined as above.

According to a preferred embodiment of the process of the invention, E is one of the following groups:

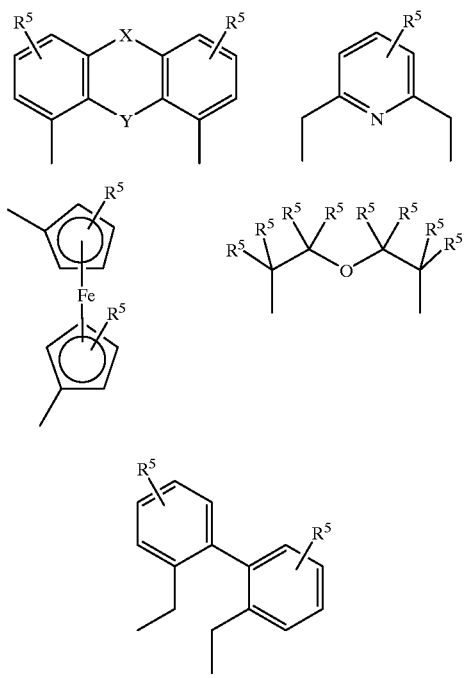

wherein X, Y, $R^5$ and $R^6$ are defined as above.

In accordance with a further preferred embodiment of the process, E is one of the following groups:

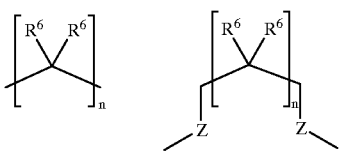

where $R^6$ is an alkyl of 1 to 8 carbon atoms or aryl of 6 to 18 carbon atoms; Z is oxygen or nitrogen; and n is between an integer of 2 to 6.

It has proved to be particularly expedient if the reaction is carried out in the presence of rhodium at a concentration of from 1 to 1000 ppm, preferably from 10 to 250 ppm, based on the total reaction mixture. The ratio of rhodium to ligand can, in this case, be between 1:1 and 1:100, preferably between 1:1 and 1:20.

The temperature during the reaction is generally between 10 and 180° C., preferably between 80 and 140° C., and the pressure is between 0.1 and 200 bar, preferably between 1 and 100 bar.

The reaction can be carried out in the presence of a solvent which may be selected from the group consisting of ether, $CO_2$, fluorinated hydrocarbons, toluene and benzene. However, the solvent can also be a polar aprotic solvent which is preferably selected from the group consisting of DMAC, DMF or NMP.

It is also possible to carry out the reaction in the presence of an oligomeric linear aldehyde, preferably particular in the presence of the trimer of the linear aldehyde to be prepared, which here also acts as solvent. Also, it has proved to be expedient to carry out the reaction in a two-phase mixture of the solvent and water.

The $CO/H_2$ ratio during the hydroformylation of the invention is usually between 1:10 and 10:1, preferably between 1:2 and 2:1.

In the following examples, there are described preferred embodiments to illustrate the invention. However, it should be understood that the invention is not intended to be limited to the specific embodiments.

EXAMPLES

General Synthesis Method

All experiments are carried out using standard Schlenk techniques under an argon atmosphere. The chemical were obtained from Acros Chimica and Aldrich Chemical Company. $Rh(CO)_2$(dipivaloyl methanoate) was prepared by the processes described in the literature (H. T. Teunissen, F. Bickelhaupt "*Phosphor, Sulfur*" 1996 118, pp. 309–312; H. K. A. C. Coolen, P. W. N. M. van Leeuwen, R. J. M. Nolte "*J. Org. Chem.*" 1966, 61, pp. 4739–4747). The NMR measurements were carried out using a Bruker AMX 300 spectrometer.

Preparation of the Diphosphine Ligands 2a–2c:

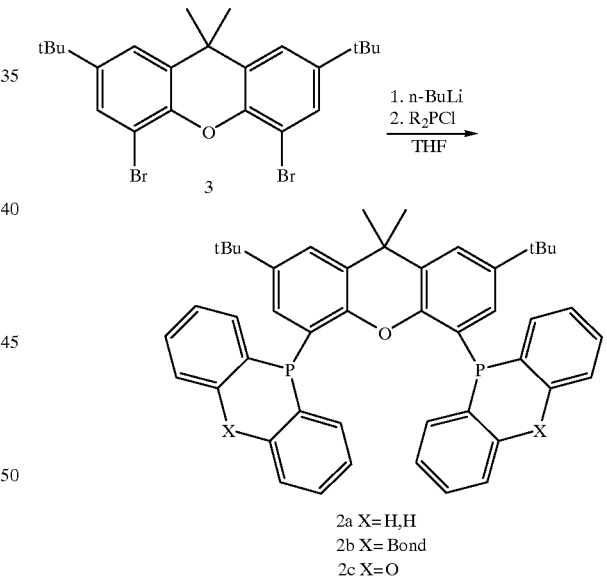

2a X=H,H
2b X=Bond
2c X=O 3.7 ml of a solution of N-butyllithium in hexane (2.5 mol, 9.3 mmol) were added to a mixture of 2.00 g of 4,5-dibromo-2,7-di-t-butyl-9,9-dimethylxanthene (compound 3) (4.16 mmol) in 50 ml of THF at −60° C. After the resultant white suspension had been stirred for 2 hours, 2.2 equivalents of chlorophosphine in 25 ml of toluene were added. The reaction mixture was slowly heated to ambient temperature and was stirred overnight. The solvent was removed under vacuum and the residue was dissolved in a mixture of toluene and saturated sodium chloride solution in a ratio of 2:1. The organic phase was removed and the aqueous phase was extracted three times with toluene. After the combined organic extracts had been dried under vacuum and the resultant residue had been washed with hexane, a white powder was isolated. The ligands were obtained in pure form after recrystallization; 2a from ethanol (yield 64%), 2b from DCM (yield 52%) and 2c from toluene (yield 75%).

The physical parameters of the resultant compounds are reproduced below:

Properties of 2a
mp.: 194–195° C.
$^1$H-NMR (in CDCl$_3$):
δ[ppm]=7.38 (d, $^4$J(H,H)=2.2 Hz, 2H; H$^{1.8}$), 7.24 (m, 20H; phenyl), 6.53 (bd, $^4$J(H,H)=2.1 Hz, 2H; H$^{3.6}$), 1.68 (s, 6H; CH$_3$), 1.11 (s, 18H; t=butyl).
$^{13}$C{$^1$H}-NMR (in CDCl$_3$):
δ[ppm]=150.7 (t, J(P,C)=19.1 Hz; CO), through-space P—P coupling=25.2 Hz, 145.4 (C$^{2.7}$), 137.0 (t, J(P,C)=13.1 Hz; PC), 134.2 (t, J(P,C)=20.4 Hz; PCCH); 129.7 (C$^{3.6}$), 129.1 (CC$^9$), 128.3 (d, J(P,C)=6.0 Hz; PCCHCH), 128.3 (PCCHCHCH), 124.9 (t, J(P,C)=18.9 Hz; C$^{4.5}$), 123.2 (C$^{1.8}$), 35.1 (C$^9$), 34.7 (C(CH$_3$)$_3$), 32.4 (C$^9$CH$_3$), 31.5 (C(CH$_3$)$_3$).
$^{31}$P{$^1$H}-NMR (in CDCl$_3$):
δ[ppm]=−16.2

| Elemental analysis: | | |
|---|---|---|
| Calculated: | C 81.78% | H 6.69% |
| Found: | 81.71% | 7.01% |

Properties of 2b
mp.: 330°
$^1$H-NMR (in CDCl$_3$):
δ[ppm]=8.35 (dd, $^3$J(H,H)=7.5 Hz, $^4$J(H,H)=1.6 Hz, 4H; DBP-H$^1$), 7.97 (d, $^3$J(H,H)=7.5 Hz, 4H; DBP-H$^4$), 7.49 (dt, $^3$J(H,H)=7.5 Hz, $^4$J(H,H)=1.4 Hz, 4H; DBP-H$^2$), 7.41 (dt, $^3$J(H,H)=7.4 Hz $^4$J(H,H)=1.3 Hz, 4H; DBP-H$^3$), 7.38 (d, $^4$J(H,H)=2.4 Hz, 2H; H$^{1.8}$), 6.76 (dt, $^4$J(H,H)=2.3 Hz, J(P,H)=2.5 Hz, 2H; H$^{3.6}$), through-space P—P coupling=37.8 Hz, 1.69 (s, 6H; CH$_3$), 1.12 (s, 18H; t-butyl).
$^{13}$C{$^1$H}-NMR (in CDCl$_3$):
δ[ppm]=151.0 (t, J(P,C)=19.6 Hz; CO), 146 (C$^{2.7}$), 144.1 (PCC), 142.5 (t, J(P,C)=4.5 Hz; P,C), 131.9 (t, J(P,C)=26.4 Hz; DBP-C$^4$); 129.5 (CC$^9$), 128.7 (DBP-C$^2$), 127.5 (t, J(P,C)=3.0 Hz; DBP-C$^3$), 126.5 (C$^{3.6}$), 124.5 (C$^{1.8}$), 124.5 (m, J(P,C)=25.7 Hz; C$^{4.5}$), 121.6 (DBP-C$^1$), 35.1 (C$^9$), 34.9 (C(CH$_3$)$_3$), 33.2 (C$^9$CH$_3$), 31.6 (C(CH$_3$)$_3$).
$^{31}$P{$^1$H}-NMR (in CDCl$_3$):
δ[ppm]=−20.8

| Elemental analysis: | | |
|---|---|---|
| Calculated: | C 81.54%, | H 5.73% |
| Found: | 82.19% | 6.46% |

Properties of 2c
mp.: 336–338° C.
$^1$H-NMR (in CDCl$_3$:
δ[ppm]=8.18 (t, $^3$J(H,H)=7.2 Hz, $^3$J(P,H)=14.4 Hz, 4H; PP—H$^1$), through-space P—P coupling=65 Hz, 7.40 (dt, $^3$J(H,H)=7.7 Hz, $^4$J(H,H)=1.3 Hz, 4H; PP—H$^3$, 7.26 (s, 2H; H$^{1.8}$), 7.24 (d, $^3$J(H,H)=8.2 Hz, 4H; PP—H$^4$), 7.17 (t, $^3$J(H,H)=7.3 Hz, 4H; PP—H$^2$), 6.67 (s, 2H; H$^{3.6}$), 1.55 (s, 6H; CH$_3$), 1.10 (s, 18H; t-butyl).
C{$^1$H}-NMR (CDCl$_3$):
δ[ppm]=155.8 (PP—CO), 149.6 (t, J(P,C)=21.3 Hz; CO), 145.1 (C$^{2.7}$), 135.5 (t, J(P,C)=43.1 Hz; PP—C$^1$), 130.5 (PP—C$^3$), 128.8 (CC$^9$), 128.5 (C$^{3.6}$), 125.7 (t, J(P,C)=29.0 Hz; PP—PC), 123.8 (C$^{1.8}$), 123.3 (t, J(P,C)=11.1 Hz; PP—C$^2$), 118.3 (C$^{4.5}$), 117.4 (PP—C$^4$), 34.4 (C$^9$), 34.1 (C(CH$_3$)$_3$), 32.7 (C$^9$CH$_3$), 30.9 (C(CH$_3$)$_3$.
$^{31}$P{$^1$H}-NMR (CDCl$_3$):
δ[ppm]=−69.9

| Elemental analysis: | | |
|---|---|---|
| Calculated: | C 78.47%, | H 5.6% |
| Found: | 78.53% | 6.17% |

The diphosphine ligands 2a, 2b and 2c described above were used in the hydroformylation of internal olefins in accordance with the conditions described below:

The reactions were carried out in a 180 ml stainless steel autoclave in toluene at 80° C. under a CO/H$_2$ atmosphere (ratio 1:1) at an initial pressure of 20 bar. The catalyst precursor was Rh(CO$_2$) (dipivaloyl methanoate), the rhodium concentration was 1.0 mmol, and the ratio of Rh:P:1-octene was 1:10:673. The conversion, the l/b ratio and the selectivities for the isomerized olefins and the linear aldehyde were determined by gas chromatography, using decane as internal standard.

TOF here denotes the turnover frequency which is calculated as (moles of aldehyde) (moles of catalyst)$^{-1}$(h)$^{-1}$.

TABLE 1

Results of hydroformylation of 1-octene:

| Ligand | t (min) | Conversion (%) | Selectivity (isomers in %) | l/b | Selectivity (lin. aldehyde in %) | TOF |
|---|---|---|---|---|---|---|
| PPh$_3$ | 5.3 | 26 | 1.2 | 3.1 | 74 | 1880 |
| 2a | 30 | 21 | 3.9 | 49 | 94 | 250 |
| 2b | 24 | 28 | 16 | 65 | 83 | 360 |
| 2c | 8.5 | 27 | 13 | 68 | 86 | 1100 |

TABLE 2

Results of hydroformylation of trans 2- and 4-octene:

| Ligand | Substrate | t (h) | Conversion (%) | l/b | Selectivity (lin. aldehyde in %) | TOF |
|---|---|---|---|---|---|---|
| 2b | 2-octene | 1.0 | 10 | 9.5 | 90 | 65 |
| 2c | 2-octene | 1.0 | 22 | 9.2 | 90 | 112 |
| 2b | 4-octene | 17 | 54 | 6.1 | 86 | 15 |
| 2c | 4-octene | 17 | 67 | 4.4 | 81 | 20 |

The reaction conditions were identical to those of Table 1, except that the temperature was 120° C. and the pressure was 2 bar.

TABLE 3

Results of hydroformylation of n-octene mixture:

| Ligand | t (h) | Conversion (%) | l/b | Selectivity (lin. aldehyde) in %) | TOF |
|---|---|---|---|---|---|
| PPh$_3$ | 2.8 | 57 | 0.5 | 33 | 318 |
| 2c | 2.8 | 63 | 1.8 | 64 | 393 |
| 2c[a] | 2.0 | 66 | 1.4 | 58 | 517 |
| 2c | 1.7 | 68 | 1.7 | 63 | 648 |

[a]Pressure 20 bar.

The reaction conditions were identical to those of Table 2 except that the pressure was 10 bar.

TABLE 4

| | | Results of hydroformylation of n-butene mixture: | | | |
|---|---|---|---|---|---|
| Ligand | t (h) | Conversion (%) | l/b | Selectivity (lin. aldehyde in %) | TOF |
| 2c | 1,5 | 82 | 6,7 | 87 | 985 |
| 2c[a] | 1,5 | 84 | 4,6 | 82 | 1050 |

[a]Pressure 20 bar.

The reaction conditions were identical to those of Table 2 except that the pressure was 10 bar.

Various modifications of the products and process of the invention may be made without departing from the spirit or scope thereof and it is to be understood that the invention is to be limited only as defined in the appended claims.

What we claim is:

1. A bidentate phosphine ligand of the formula

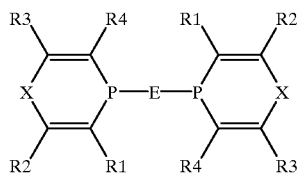

I wherein $R_1$, $R_2$, $R_3$ and $R_4$ together form at least one aliphatic or aromatic ring, E is selected from the group consisting of

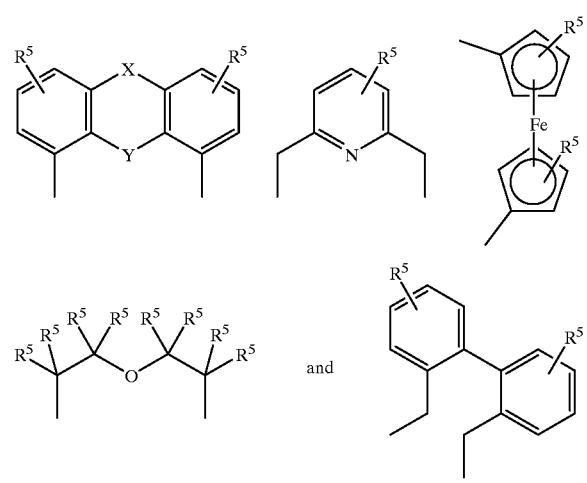

and

X is

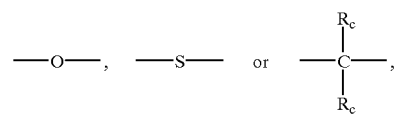

Y is oxygen or sulfur, $R_c$ is selected from the group consisting of hydrogen, alkyl of 1 to 8 carbon atoms, aryl of 6 to 18 carbon atoms and aryloxy of 6 to 18 carbon atoms and $R_5$ is alkyl of 1 to 8 carbon atoms or aryl of 6 to 18 carbon atoms.

2. A process for the preparation of a linear aldehyde comprising hydroformylating an internal olefin of 4 to 12 carbon atoms with carbon monoxide and hydrogen in the presence of bidentate phosphine ligand of claim 1.

3. The process of claim 2 wherein the reaction is carried out in the presence of 1 to 1000 ppm of rhodium based on the total reaction mixture.

4. The process of claim 3 wherein rhodium is present at 10 to 250 ppm.

5. The process of claim 3 wherein the ratio of rhodium to ligand is 1:1 to 1:100.

6. The process of claim 3 wherein the ratio of rhodium to ligand is 1:1 to 1:20.

7. The process of claim 2 wherein the hydroformylation is effected at 10 to 180° C.

8. The process of claim 2 wherein the hydroformylation is effected at 80 to 140° C.

9. The process of claim 2 wherein the reaction is effected at a pressure of 0.1 to 200 bar.

10. The process of claim 2 wherein the hydroformylation is effected in the presence of a solvent selected from the group consisting of ether, carbon dioxide, fluorinated hydrocarbons, toluene and benzene.

11. The process of claim 2 wherein the hydroformylation is effected in a polar aprotic solvent selected from the group consisting of dimethylformamide, dimethylacetamide and N-methylpyrrolidone.

12. The process of claim 12 wherein the hydroformylation is effected in the presence of an oligomeric aldehyde.

13. The process of claim 9 wherein the oligomeric aldehyde is the trimer of the aldehyde to be formed.

14. The process of claim 7 wherein the hydroformylation is effected in a two phase with water.

15. The process of claim 2 wherein the ratio of carbon monoxide to hydrogen is 1:10 to 10:1.

16. The process of claim 2 wherein the ratio of carbon monoxide to hydrogen is 1:2 to 2:1.

* * * * *